United States Patent [19]

Tilly et al.

[11] 4,225,577
[45] Sep. 30, 1980

[54] IONIC POLYIODO BENZENE DERIVATIVES USEFUL AS X-RAY CONTRAST MEDIA

[75] Inventors: Guy Tilly; M. Jean-Charles Hardouin; Jean Lautrou, all of Aulnay-sous-Bois, France

[73] Assignee: Guerbet S.A., Aulnay-sous-Bois, France

[21] Appl. No.: 43,046

[22] Filed: May 29, 1979

[30] Foreign Application Priority Data

May 31, 1978 [GB] United Kingdom ............... 24828/78

[51] Int. Cl.² ..................... A61K 29/02; C07C 101/72
[52] U.S. Cl. ........................................... 424/5; 560/42; 562/451
[58] Field of Search ............... 560/42; 562/451; 424/5

[56] References Cited

U.S. PATENT DOCUMENTS

| | | | |
|---|---|---|---|
| 3,732,293 | 5/1973 | Ackerman | 560/42 |
| 3,803,221 | 4/1974 | Ackerman | 424/5 |
| 3,939,204 | 2/1976 | Buttermann | 424/5 |
| 4,107,286 | 8/1978 | Tilly et al. | 560/42 |

*Primary Examiner*—G. T. Breitenstein
*Attorney, Agent, or Firm*—Young & Thomspon

[57] ABSTRACT

This invention relates to compounds of the formula (I):

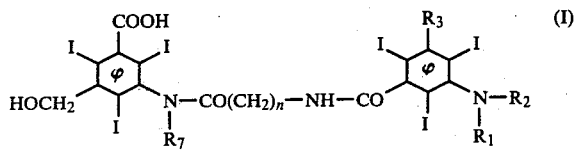

in which:
n is an integer from 1 to 5 inclusive,
$R_1$ represents a hydrogen atom or a $C_{1-4}$ alkanoyl group,
$R_2$ represents a hydrogen atom, a $C_{1-4}$ alkanoyl group, or a $C_{1-4}$ alkyl group,
$R_3$ represents a hydrogen atom, a group of the formula

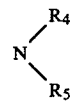

or of the formula $-CONHR_6$, in which:
$R_4$ represents a hydrogen atom or a $C_{1-4}$ alkanoyl group,
$R_5$ represents a hydrogen atom or a $C_{1-4}$ alkanoyl group, or a $C_{1-4}$ alkyl group,
$R_6$ represents a hydrogen atom or a $C_{1-4}$ alkyl group,
$R_7$ represents a hydrogen atom or a methyl group, and their $C_{1-4}$ alkyl esters and their salts with pharmaceutically acceptable bases.

Said compounds are useful as X-ray contrast media.

6 Claims, No Drawings

IONIC POLYIODO BENZENE DERIVATIVES USEFUL AS X-RAY CONTRAST MEDIA

This invention relates to new ionic polyiodo benzene derivatives useful as X-ray contrast media.

This invention relates more particularly to new compounds having two trio-iodo benzene nuclei and a single carboxylic group.

Thus, this invention relates to new compounds having the general formula:

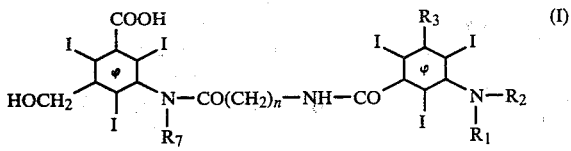

in which:

n is an integer from 1 to 5 inclusive, $R_1$ represents a hydrogen atom or a $C_{1-4}$ alkanoyl group, $R_2$ represents a hydrogen atom, a $C_{1-4}$ alkanoyl group or a $C_{1-4}$ alkyl group, $R_3$ represents a hydrogen atom, a group having the formula

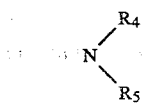

or the formula —$CONHR_6$ in which:

$R_4$ represents a hydrogen atom or a $C_{1-4}$ alkanoyl group, $R_5$ represents a hydrogen atom or a $C_{1-4}$ alkanoyl group or a $C_{1-4}$ alkyl group, $R_6$ represents a hydrogen atom or a $C_{1-4}$ alkyl group; and $R_7$ represents a hydrogen atom or a methyl group; and their $C_{1-4}$ alkyl esters and their salts with pharmaceutically acceptable bases.

Salts of acids of the formula (I) include, for example: alkali metal salts, such as sodium and potassium salts; ammonium salts; alkaline-earth metal salts, such as calcium salts; and salts with organic bases, such as ethanolamine and methylglucamine salts.

The compounds of the formula (I) may be prepared by reacting an amine having the formula:

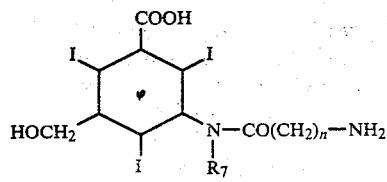

with an acid chloride having the formula:

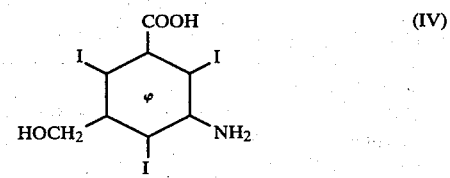

in which $R_1, R_2, R_3, R_7$ and n have the meanings given for the formula (I).

Said reaction may be effected in conventional manner, within a polar solvent such as dimethylacetamide, dimethyl sulfoxide, dimethylformamide or a water-dioxan mixture at a temperature of 20°–60° C., in the presence of excess acid binding agent, such as triethylamine or sodium carbonate. Reaction time may vary from about 2 hours to about 4 days.

The amines of the formula (II) in which $R_7$ is hydrogen may be obtained in conventional manner, by condensation of the amine having the formula:

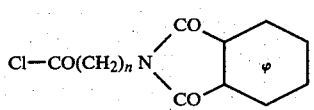

with an acid chloride having the formula:

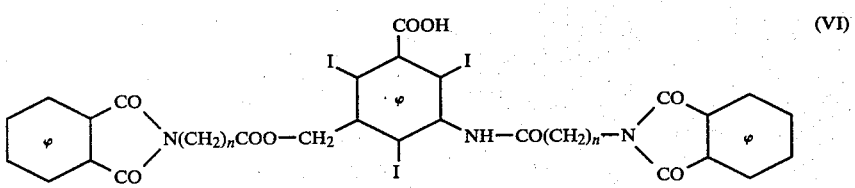

followed by hydraxinolysis of the resulting condensation product having the formula:

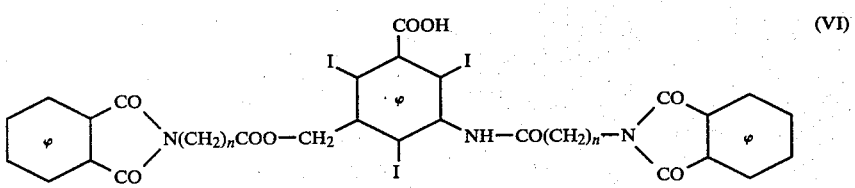

The condensation reaction of the amine of the formula (IV) with the acid chloride of the formula (V) may be effected in conventional manner, within a polar solvent such dimethylacetamide or dimethylformamide at a temperature of 20°–100° C., the acid chloride being used in an excess amount. Reaction time may vary from about 2 hours to about 4 days.

The hydrazinolysis reaction of the compound of the formula (VI) is effected according to usual techniques, by action of hydrazine in aqueous medium. A large excess of hydrazine (4–8 moles per mole of compound of the formula (VI)) is advantageously used.

The amines of the formula (II) in which $R_7$ is a methyl group may also be obtained from the amine of the formula (IV), in the following manner, comprising:

condensing the amine of the formula (IV) with an acid chloride of the formula:

$$Cl—CO(CH_2)_nCl \qquad (V)$$

according to the technique disclosed in U.S. Pat. No. 3,210,412, to give a derivative having the formula (VI):

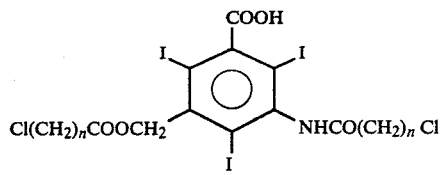

then methylating the resulting compound according to conventional techniques, to give a methylated derivative having the formula (VII):

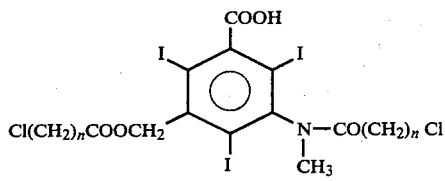

and treating the resulting compound with concentrated aqueous ammonia.

The following non-limiting Examples illustrate this invention.

EXAMPLE 1

Preparation of 2,4,6-triiodo-3-hydroxymethyl-5-(2,4,6-triiodo-3-N-methylcarbamoyl-5-N-methyl-N-acetylamino-benzoyl)glycylamino-benzoic acid

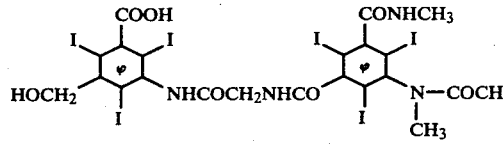

(1) Preparation of the amine of the formula (II)
1.1 Preparation of 2,4,6-triiodo-3-N-phthalimido-acetoxy-methyl-5-phthalimido-acetylamino-benzoic acid

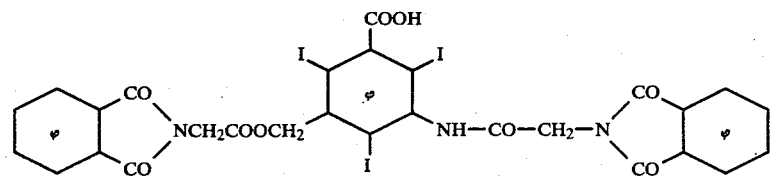

110 g (0.2 mole) 2,4,6-triiodo-3-hydroxymethyl-5-amino-benzoic acid are dissolved in 200 ml dimethylacetamide. 98 g (0.44 mole) phthalylglycine acid chloride are added thereto. The reaction mixture is stirred overnight at room temperature and is then poured over 2 liters water at 80° C. The resulting precipitate is suction filtered, after which it is washed with water at 90° C. and dried in an oven, to give 175 g of product (Yield: 95%).

Purity control: TLC on silicagel plate, in benzene/methylethylketone/formic acid 60:25:20 eluent.
$R_f$ of the starting material: 0.85
$R_f$ of the resulting product: 0.05
$R_f$ of phthalylgylcine acid: 0.77
1.2 Preparation of 2,4,6-triiodo-3-hydroxymethyl-5-amino-acetylamino-benzoic acid

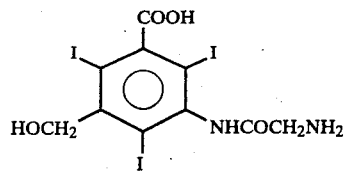

92 g (0.1 mole) of the product obtained above in 1.1 are suspended in 250 ml water and 30 g hydrazine hydrate (0.6 mole). The suspension is heated at 80° C. for 12 hours, allowed to cool to 40° C. and suction filtered at that temperature, after which the resulting material is washed with water and dried in an oven, to give 47 g of product (Yield: 78%).

Purity control: (a) TLC; Benzene/methylethylketone/formic acid 60:25:20 eluent.
$R_f$ of the starting material: 0.05
$R_f$ of the resulting product: 0.25*
*An orange-yellow spot is obtained on development with ninhydrin.
(b) Purity of the product by iodine titration: 97%.
(c) Purity of the product by titration with NaOH: 100%.

(2) Preparation of 2,4,6-triiodo-3-hydroxymethyl-5-(2,4,6-triiodo-3-N-methylcarbamoyl-5-N-methyl-N-acetylamino-benzoyl)glycylamino-benzoic acid
2.1 Condensation 40 g (0.065 mole) 2,4,6-triiodo-3-hydroxymethyl-5-aminoacetylamino-benzoic acid are suspended in a mixture of 60 ml dimethylacetamide and 21.5 ml triethyl amine. (42 g 2,4,6-triiodo-3-N-methylcarbamoyl-5-N-methyl-N-acetlyamino-benzoic acid chloride are added to this suspension and the resulting material is stirred for 12 hrs at 50° C. TLC is then used to ascertain there is less than 3% starting material left. The solution is poured over 300 ml water, the pH is adjusted at 7 if required, and the insoluble is suction filtered. The filtrate is precipitated with hydrochloric acid to markedly acidic pH, after which the precipitate is suction filtered, washed with water and dried in an oven, to give 64 g crude product (Yield: 80%).

Purity control: TLC; benzene/methylethylketone/-formic acid 60:25:20.
$R_f$ of the starting amine: 0.25
$R_f$ of the acid chloride: 0.8
$R_f$ of the condensed product: 0.4
2.2 Purification 60 g of the resulting product are dissolved in 100 ml water and sufficient 10 N sodium hydroxide, and the pH is then adjusted to 7 with acetic acid. The material is heated to 80° C. and charcoaled once, then filtered and made acidic to markedly acidic pH with dilute hydrochloric acid. The material is suction filtered, washed with water and dried in an oven, to give 53 g of product which are suspended in 75 ml 95% ethanol. The suspension is then refluxed. Complete dissolution occurs, followed by crystallization. The material is heated for a total of 48 hours, with stirring, after which it is allowed to cool, it is suction filtered and washed with ethanol. The wet product is dissolved in 200 ml water and sodium hydroxide. The pH is adjusted at 4–5 with acetic acid and the product is charcoaled 3 times. It is then filtered, and made acidic to highly acid pH with concentrated hydrochloric acid. The resulting material is suction filtered, washed with water and dried in an oven, to give 24 g pure product (Yield: 40%).

Purity control: TLC as for the condensation.

Purity of the product by titration with sodium hydroxide: 98%

Purity of the product by titration with sodium methoxide: 104%

Purity of the product by iodine titration: 97.5%

EXAMPLE 2

Preparation of 2,4,6-triiodo-3-hydroxymethyl-5-(2,4,6-triiodo-3-N-methyl-N-acetylamino-benzoyl)glycylamino-benzoic acid The procedure of Example 1 is used, except that 2,4,6-triiodo-3-N-methyl-N-acetylamino-benzoic acid chloride is used as acid chloride.

The following characteristics are obtained on TLC analysis:

| Rf/ product | eluent | Benzene/ MEC/HCOOH (60:25:20) | Butanol/H$_2$O/ CH$_3$COOH (50:25:11) | Isopropanol/ Ethyl acetate/ NH$_4$OH (35:35:40) |
|---|---|---|---|---|
| Starting amine | | 0.05 | 0.25 | 0.5 |
| Acid* | | 0.85 | 0.7 | 0.7 |
| Condensed product | | 0.6 | 0.7 | 0.65 |

*corresponding to the acid chloride

EXAMPLE 3

Preparation of 2,4,6-triiodo-3-hydroxymethyl-5-(2,4,6-triiodo-3-amino-5-N-methyl-N-acetylamino-benzoyl)glycylamino-benzoic acid The procedure of Example 1 is used, except that the acid chloride is 2,4,6-triiodo-3-amino-5-N-methyl-N-acetylamino-benzoic acid chloride.

The following characteristics are obtained on TLC analysis:

| Rf/ product | eluent | Benzene/ MEC/HCOOH (60:25:20) | Butanol/H$_2$O/ CH$_3$COOH (50:25:11) | Isopropanol/ Ethyl acetate/ NH$_4$OH (35:35:40) |
|---|---|---|---|---|
| Starting amine | | 0.05 | 0.25 | 0.5 |
| Acid* | | 0.85 | 0.7 | 0.7 |
| Condensed product | | 0.55 | 0.6 | 0.6 |

*corresponding to the acid chloride

EXAMPLE 4

Preparation of 2,4,6-triiodo-3-hydroxymethyl-5-(2,4,6-triiodo-3-N-methylcarbamoyl-5-N-methyl-N-acetylamino-benzoyl)β-aminopropionyl-amino-benzoic acid (1) Preparation of 2,4,6-triiodo-3-hydroxymethyl-5-aminopropionylamino-benzoic acid The procedure of Example 1.1 is used, with N-phthalyl-alanine acid chloride (amine of the formula (II)).

The resulting amine in benzene/methylethylketone/formic acid (60:25:20) eluent has a R$_f$ value=0.1.

(2) Preparation of the compound of the formula (I)

The compound is prepared according to the procedure of Example 1, from the amine obtained in 4.1 and the same acid chloride as in Example 1.

The following characteristics are obtained on TLC analysis:

| Rf/ product | eluent | Benzene/ MEC/HCOOH (60:25:20) | Butanol/H$_2$O/ CH$_3$COOH (50:25:11) | Isopropanol/ Ethyl acetate/ NH$_4$OH (35:35:40) |
|---|---|---|---|---|
| Starting amine | | 0.1 | 0.2 | 0.5 |
| Acid* | | 0.55 | 0.55 | 0.7 |
| Condensed product | | 0.3 | 0.55 | 0.65 |

*corresponding to the acid chloride

EXAMPLE 5

Preparation of 2,4,6-triiodo-3-hydroxymethyl-5-(2,4,6-triiodo-3-amino-5-N-methylcarbamoyl-benzoyl)glycyl-N-methylamino-benzoic acid (1) Preparation of 2,4,6-triiodo-3-hydroxymethyl-5-N-methyl-N-aminoacetamido-benzoic acid 1.1 Preparation of 2,4,6-triiodo-3-chloroacetoxymethyl-5-N-chloroacetamido-benzoic acid The compound is prepared as disclosed in U.S. Pat. No. 3,210,412, from the amine of the formula (II)(2,4,6-triiodo-3-hydroxymethyl-5-amino-benzoic acid).

Purity control: TLC: eluent: n-Butanol/acetic acid/water (50:11:25).

R$_f$ of the starting material: 0.6
R$_f$ of the product obtained: 0.7

1.2 Preparation of 2,4,6-triiodo-3-hydroxymethyl-5-N-methyl-N-chloroacetamido-benzoic acid 698 g (1 mole) of the preceding compound are dissolved in 3.3 moles 5 N sodium hydroxide. Methyl iodide (1.3 mole) is added dropwise thereto, while maintaining the temperature below 10° C. by means of an ice bath. After stirring for 20 hours at room temperature, the reaction solution is poured over 2 liters dilute (10%) hydrochloric acid. The resulting precipitate is suction filtered, washed with water and dried in an oven at 50° C., to give 563 g of product (Yield: 88.5%).

Purity control: TLC: eluent: n-Butanol/acetic acid/water (50:11:25).

R$_f$ of the starting material: 0.7
R$_f$ of the product obtained: 0.5

1.3 Preparation of 2,4,6-triiodo-3-hydroxymethyl-5-N-methyl-N-aminoacetamido-benzoic acid 560 g (0.8 mole) of the previously prepared acid are dissolved in 4.5 liters concentrated aqueous ammonia.

Complete dissolution occurs and the resulting solution is heated at 60° C. for 48 hours, after which it is concentrated to 0.5 liter, in vacuo. The crystalline ammonium salt is suction filtered, redissolved in 500 ml water and a sufficient amount of sodium hydroxide, and is then reprecipitated with acetic acid at pH 4. The material is suction filtered, repeatedly washed with water and dried in an oven, to give 394 g of product (Yield: 80%).

Purity control: TLC: eluent: ethyl acetate/isopropanol/aqueous ammonia (55:35:20).

$R_f$ of the starting material: 0.55

$R_f$ of the product obtained: 0.35 (development: yellow colour with ninhydrin).

(2) Preparation of the compound of the formula (I)

The compound of the formula (I) is prepared by the procedure of Example 1, from the amine obtained in 5.1 and 2,4,6-triiodo-3-amino-5-N-methylcarbamoyl-benzoic acid chloride.

The following characteristics are obtained on TLC analysis:

| Rf/product | eluent Benzene/ MEC/HCOOH (60:25:20) | Butanol/H$_2$O/ CH$_3$COOH (50:25:11) | Isopropanol/ Ethyl acetate/ NH$_4$OH (35:35:40) |
|---|---|---|---|
| Derivative chloroacetylated prior to aminolysis | 0.8 | 0.75 | 0.75 |
| Starting amine | 0.2 | 0.4 | 0.7 |
| Acid* | 0.75 | 0.6 | 0.65 |
| Condensed product | 0.5 | 0.6 | 0.75 |

*corresponding to the acid chloride

The compounds of the formula (I) are useful as X-ray contrast media.

The preferred pharmaceutical form consists of aqueous solutions of salts of compounds of the formula (I).

The aqueous solutions contain advantageously 5–100 g salt per 100 ml, and the injectable amount of such solutions may vary from 5 ml to 1000 ml.

Having now described our invention what We claim as new and desire to secure by Letters Patent is:

1. A compound selected from the compounds of the formula (I):

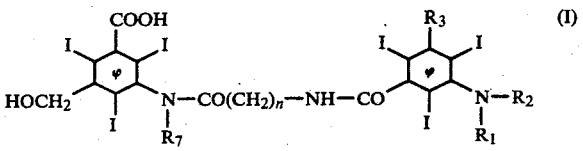

in which:
n is an integer from 1 to 5 inclusive,
$R_1$ is selected from hydrogen and $C_{1-4}$ alkanoyl,
$R_2$ is selected from hydrogen, $C_{1-4}$ alkanoyl and $C_{1-4}$ alkyl,
$R_3$ is selected from hydrogen, a group of the formula

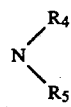

and a group of the formula —CONHR$_6$, in which:
$R_4$ is selected from hydrogen and $C_{1-4}$ alkanoyl,
$R_5$ is selected from hydrogen, $C_{1-4}$ alkanoyl and $C_{1-4}$ alkyl,
$R_6$ is selected from hydrogen and $C_{1-4}$ alkyl,
$R_7$ is selected from hydrogen and methyl, and
$C_{1-4}$ alkyl esters thereof and a salt thereof with pharmaceutically acceptable bases.

2. Compounds as claimed in claim 1, wherein $R_7$ is a hydrogen atom.

3. Compounds as claimed in claim 1, wherein $R_7$ is a methyl group.

4. X-ray contrast medium, comprising an effective amount of a compound of the formula (I) as defined in claim 1, in a pharmaceutically acceptable carrier.

5. X-ray contrast medium as claimed in claim 4, comprising an effective amount of an aqueous solution of a phrmaceutically acceptable salt of a compound of the formula (I).

6. X-ray contrast medium as claimed in claim 5, comprising an aqueous solution containing 5–100 g of a salt of a compound of the formula (I) per 100 ml of solution.

* * * * *